US006998613B2

(12) United States Patent
Syllaios et al.

(10) Patent No.: US 6,998,613 B2
(45) Date of Patent: Feb. 14, 2006

(54) INTEGRATED SPECTROSCOPIC MICROBOLOMETER WITH MICROFILTER ARRAYS

(75) Inventors: Athanasios J. Syllaios, Richardson, TX (US); Prem Chahal, Plano, TX (US)

(73) Assignee: Raytheon Company, Waltham, MA (US)

( * ) Notice: Subject to any disclaimer, the term of this patent is extended or adjusted under 35 U.S.C. 154(b) by 54 days.

(21) Appl. No.: 10/421,477

(22) Filed: Apr. 22, 2003

(65) Prior Publication Data

US 2004/0211901 A1 Oct. 28, 2004

(51) Int. Cl.
G01J 5/02 (2006.01)
(52) U.S. Cl. ................................. 250/339.02
(58) Field of Classification Search ........... 250/339.02, 250/338.1, 345
See application file for complete search history.

(56) References Cited

U.S. PATENT DOCUMENTS

| 6,028,312 A * | 2/2000 | Wadsworth et al. ........ 250/351 |
| 6,064,066 A | 5/2000 | Bevan et al. ............... 250/345 |
| 6,160,257 A | 12/2000 | Deb ......................... 250/338.1 |
| 6,441,368 B1 | 8/2002 | Grinberg et al. ............ 250/239 |
| 2002/0175284 A1 | 11/2002 | Vilain ....................... 250/338.1 |

OTHER PUBLICATIONS

Kwa et al., "Backside-Illuminated Silicon Photodiode Array for an Integrated Spectrometer," IEEE Transactions on Electron Devices, vol. 44, No. 5, pp. 761-765, May 1997.
Gittins et al., "LWIR Multispectral Imaging Chemical Sensor," Proceedings of SPIE, 11 pages, Nov. 1-5, 1998.
PCT Search Report for PCT/US2004/010510 with PCT Written Opinion, 12 pages, Aug. 26, 2004.

* cited by examiner

Primary Examiner—David Porta
Assistant Examiner—Marcus Taningco
(74) Attorney, Agent, or Firm—Baker Botts L.L.P.

(57) ABSTRACT

A method for forming an integrated circuit includes providing an array of detectors proximate an outer surface of a first substrate layer. The array of detectors operate to detect the presence or absence of one or more wavelengths within a spectrum of transmitted energy. One or more filters are provided proximate a second substrate layer. The one or more filters operate to affect the spectrum of transmitted energy through the one or more filters. The second substrate layer is proximate to the outer surface of the first substrate layer to enclose the array of detectors in a vacuum environment.

39 Claims, 5 Drawing Sheets

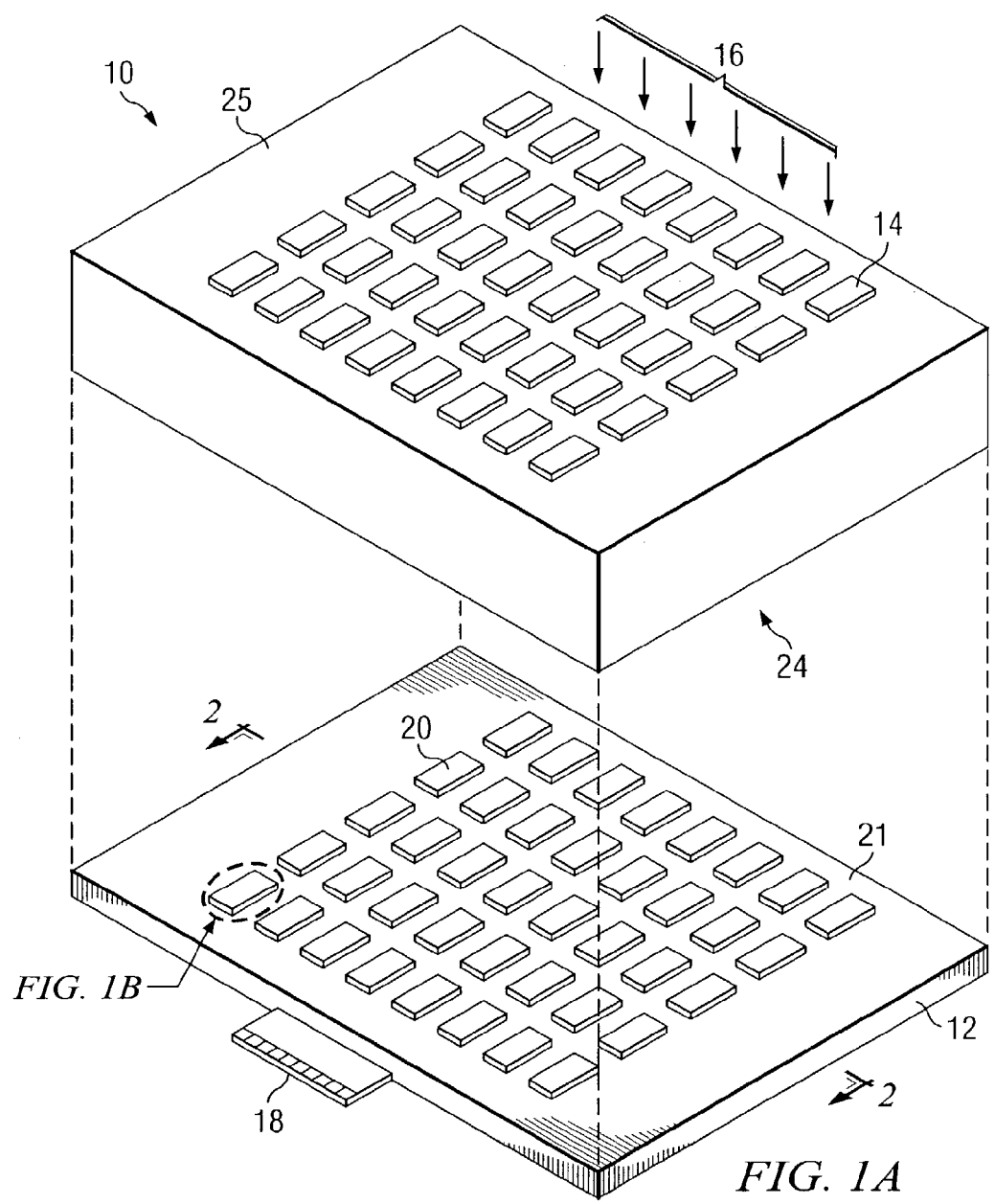
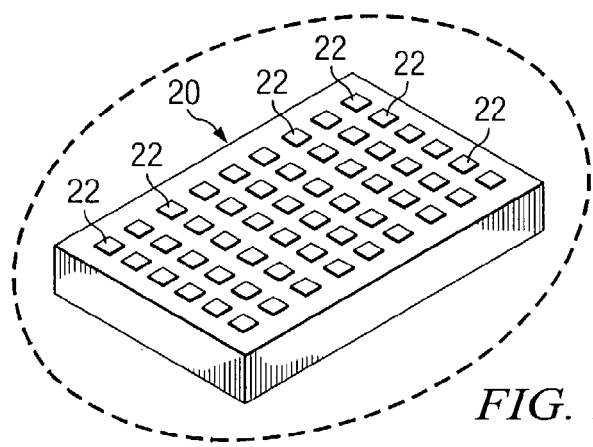
FIG. 1A
FIG. 1B

INTEGRATED SPECTROSCOPIC MICROBOLOMETER WITH MICROFILTER ARRAYS

TECHNICAL FIELD OF THE INVENTION

This invention relates generally to the field of integrated circuits and, more particularly, to integrated spectroscopic microbolometers including microfilter arrays.

BACKGROUND OF THE INVENTION

The detection of particular wavelengths or wavelength ranges within a spectrum of infrared light is useful for both the creation of imagery and for spectroscopy. For the creation of imagery, a filter may be placed in front of an optical detector, and energy such as infrared light, may be directed through the filters to the optical detector. The filters may operate to block a particular wavelength or wavelength range within the spectrum of infrared light and to allow all other wavelengths to pass through the filter for detection by the optical detector. Conversely, the filters may operate to allow a particular wavelength or wavelength range to pass through the filters while blocking all other wavelengths. In either situation, the infrared light may be translated into monochromatic or polychromatic imagery.

Additionally, specialized spectroscopic filters may be used in conjunction with optical detectors to detect exposure to vapors, chemicals, gases, or biological agents. Typically, filters used for imagery and spectroscopy are mechanically controlled filters or filter wheels that are large and bulky. As such, existing spectroscopic and imagery systems may be incompatible with integrated circuits, such as microelectromechanical systems (MEMS), and are not easily portable for the immediate in-field detection of poisonous gases and other vapors, chemicals, gases, or biological agents.

SUMMARY OF EXAMPLE EMBODIMENTS

In accordance with the present invention, disadvantages and problems associated with methods of forming spacer layers are reduced or eliminated.

According to one embodiment of the present invention, a method for forming an integrated circuit includes providing an array of detectors proximate an outer surface of a first substrate layer. The array of detectors operate to detect the presence or absence of one or more wavelengths within a spectrum of transmitted energy. One or more filters are provided proximate a second substrate layer. The one or more filters operate to affect the spectrum of transmitted energy through the one or more filters. The second substrate layer is proximate to the outer surface of the first substrate layer to enclose the array of detectors in a vacuum environment.

Depending on the specific features implemented, particular embodiments of the present invention may exhibit some, none, or all of the following technical advantages. A technical advantage of one exemplary embodiment of the present invention is the detection of vapors, chemicals, gases, and biological agents, such as carbon monoxide, various toxins and viruses, volatile organic compounds, and chemical warfare agents, pollutants, and industrial gases. Another technical advantage is that filters used in the detection of such gases or biological agents may be integrated into integrated circuits also performing multi-spectrum imagery. Moreover, both spectroscopic systems and imagery systems may correspond to a single detector array in an integrated circuit. If such filters are mounted on the outside of the integrated circuit, another technical advantage is that the filters may be easily replaced allowing the integrated circuit portion of the system to be reused. Another technical advantage of one exemplary embodiment of the present invention is the mass production of microbolometer detector arrays that may be customized to detect particular vapors, chemicals, gases, or biological agents through replaceable filter arrays. Additionally, the resulting systems are small enough to be incorporated into microelectromechanical systems (MEMS) and may be portable for the infield detection and measurement of vapors, chemicals, gases, and biological agents.

Other technical advantages may be readily apparent to one skilled in the art from the figures, descriptions and claims included herein. None, some, or all of the examples may provide technical advantages.

BRIEF DESCRIPTION OF THE DRAWINGS

For a more complete understanding of the present invention and its features and advantages, reference is now made to the following description, taken in conjunction with the accompanying drawings, in which:

FIG. 1A is a simplified schematic drawing of a spectroscopic system that includes a detector array positioned proximate to one or more filters in accordance with one embodiment of the present invention;

FIG. 1B is a simplified schematic diagram of a detector that may be included within the spectroscopic system;

DETAILED DESCRIPTION OF EXAMPLE EMBODIMENTS

Figure 2:
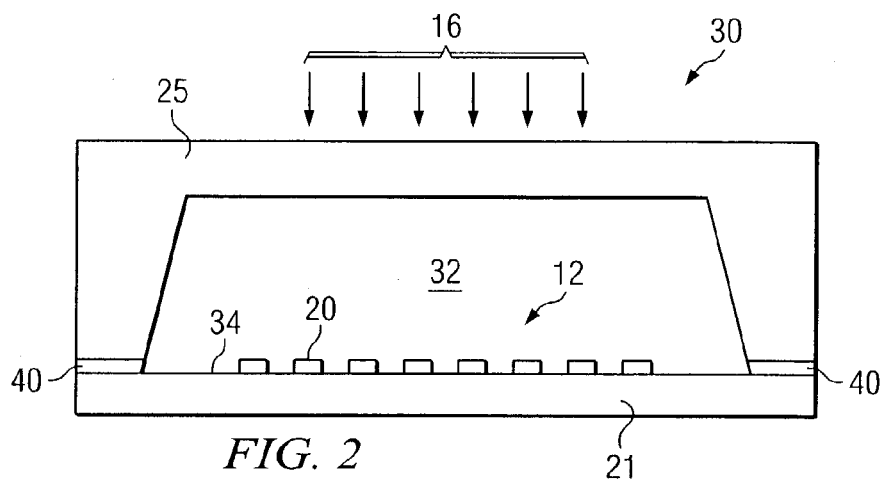
FIG. 2 is a cross-sectional view of an integrated circuit structure that includes a detector array within a vacuum.

FIG. 1A is a simplified schematic drawing illustrating the components of an example spectroscopic system 10 that includes a detector array 12 positioned proximate to one or more filters 14. Integration of the one or more filters 14 allows miniaturization of spectroscopic system 10 such that spectroscopic system 10 may be integrated into microelectromechanical (MEMS) systems. In operation, radiant energy 16, such as infrared light, is transmitted through spectroscopic system 10 to determine the presence or absence of one or more wavelengths within the spectrum of transmitted energy 16. An indication of the presence or absence of a particular wavelength or wavelength range may then be transmitted to readout circuitry 18 and may be used to create imagery and/or to detect biological agents or gases.

Detector array 12 includes at least one row of N detectors 20 on an integrated circuit substrate 21. Each detector 20 may be further divided into a sub-array of micro-detectors 22 as illustrated by an example schematic diagram provided by FIG. 1B. Detectors 20 and micro-detectors 22 may be classified in various ways. For example, detectors 20 and micro-detectors 22 may include single detectors, i.e. pixel arrays, wavelength detectors, thermal detectors or any other detector for detecting transmitted energy 16. Typically, multiple detectors 20 or micro-detectors 22 may detect each pixel in an array of pixels for image detection. Alternatively, each detector 20 or micro-detector 22 may include one pixel in an array of pixels. Each detector 20 or micro-detector 22 may include a single detector for chemical analysis by spectral absorption. Detectors relying upon the change in resistivity due to photon heating are called bolometers. In particular embodiments, detector array 12 may include an array of bolometer structures made of hydrogenated amorphous silicon, vanadium oxide, amorphous silicon carbide, high temperature superconductors (e.g., Yttrium Barium Copper Oxide), titanium or other metals, Indium Antimonide or other semiconductors, or other suitable material. Each bolometer may detect a single pixel in a two-dimensional image from infrared light or may detect visible light and near ultraviolet light by recognizing the presence or absence of a particular wavelength or wavelength range. Other types of detectors are photon detectors, such as photo conductors, photo diodes, and photo transistors.

One or more filters 14 are positioned adjacent or proximate to detector array 12. In particular embodiments, one or more filters 14 may be included in a filter array 24 that includes at least one row of M filters 14. As will be described in greater detail with regard to FIGS. 3A through 3B, filters 14 may be integrated or positioned proximate to a second substrate layer 25 that forms a lid over detector array 12. Although the number of filters 14 may correspond to the number of detectors 20 (i.e., M=N), the number of filters 14 and detectors 20 need not necessarily be equal. Accordingly, each filter 14 may correspond to two or more detectors 20 (M<N). Alternatively, a single detector 20 may correspond to two or more filters 14 (M>N). Several filters 14 may be used in combination to measure data in a specific bandwidth region.

Each filter 14 operates to affect the spectrum of transmitted energy 16 through filter 14. In various embodiments, one or more filters 14 are selectively transmissive and may be selectively transmissive with respect to narrow bands of wavelengths of radiant energy. If for example, filter 14 blocks the transmission of all wavelengths of energy 16 outside of a particular wavelength range, filter 14 affects the spectrum of transmitted energy 16 by blocking all other wavelengths and allowing only that portion of energy 16 falling within the particular wavelength range to pass through filter 14. Alternatively, filters 14 may operate to block wavelengths within a particular wavelength range and allow all other wavelengths to pass through filter 14. Accordingly, filters 14 react to change the transmissivity of energy 16 through spectroscopic system 10. In various embodiments, filters 14 may also be selectively reactive to particular biological agents or gases. For example, filters 14 may be reactive to gases such as carbon monoxide, hydrogen sulfide and ozone. Filters 14 may additionally or alternatively be reactive to volatile organic compounds (VOC), chemical warfare agents, pollutants, industrial gases, various toxins and viruses, or other biological agents. Thus, filters 14 may react by changing the transmissivity of energy 16 by filtering specific wavelengths of energy 16 when the presence of a particular biological agent or gas is present in the immediate environment. To indicate the detection of such gases or agents in the immediate environment, otherwise clear filters 14 may turn cloudy. Alternatively, otherwise cloudy filters 14 may turn clear. Since biological agents and gases radiate or absorb at known wavelengths, filters 14 and spectroscopic system 10 may also be used for the remote detection of biological agents and gases outside the immediate environment of spectroscopic system 10.

Although read-out circuitry 18 is depicted as being mounted proximate to detector array 12 on the same integrated circuit substrate 21 supporting detector array 12, it is recognized that read-out circuitry 18 may be mounted to the integrated circuit in any other appropriate manner. Read-out circuitry 18 couples system 10 to a processor or other computing device to produce multi-spectrum imagery. If, for example, detector array 12 detects the absence or presence of a particular wavelength in the spectrum of transmitted energy 16, a processor may translate the particular wavelength into imagery by recording and storing image intensity levels on a pixel by pixel basis from detector array 12. Where such filters 14 in filter array 24 are capable of spectroscopy and detect a target gas or biological agent, a processor may trigger an alarm to warn of the presence or absence of the agent or gas. Because filter 14 may be integrated into an integrated circuit such as a microelectromechanical system (MEMS), spectroscopic system 10 is capable of potentially life-saving in-field detection of vapors, chemicals, gasses, or biological agents.

In operation, transmitted energy 16 such as infrared light is directed at filters 14. As transmitted energy 16 passes through the one or more transmissive filters 14, the one or more filters 14 may affect the spectrum of transmitted energy 16 through the one or more filters 14. For example, filters 14 may block the transmission of all energy 16 within a particular wavelength range. Alternatively, filters 14 may block energy 16 outside the particular wavelength range. Additionally or alternatively, the transmissivity of particular filters 14 may be affected by reactions with particular biological agents or gases in the surrounding environment.

After passing through filters 14, transmitted energy 16 is directed toward detector array 12. Detector array 12 may recognize the presence of a particular wavelength or wavelength range that has passed through filters 14. Alternatively, detector array 12 may recognize the absence of a particular wavelength or wavelength range. As described above, the information gathered by detector array 12 may be transmitted via read-out circuitry 18 to a processor. The processor may use the information to generate imagery and/or to trigger alarms.

FIG. 2 is a cross-sectional view of an example integrated circuit structure 30 that includes detector array 12 disposed within a vacuum 32. FIG. 2 is a view of spectroscopic system 10 along the 2—2 axis of FIG. 1A. Detector array 12 is provided proximate an outer surface 34 of a first substrate layer 21. First substrate layer 21 may comprise any suitable material used in integrated circuit fabrication, such as silicon, germanium, gallium arsenide, or other suitable material. For purposes of teaching aspects of the present invention, an exemplary embodiment will be described that uses a first substrate layer 21 comprising silicon. In particular embodiments, first substrate layer 21 is on the order of 600–700 microns in thickness.

Integrated circuit structure 30 also includes a second substrate layer 25 positioned proximate to detector array 12 and first substrate layer 21. Second substrate layer 25 is bonded to outer surface 34 of first substrate layer 21 at the first and second substrate layer interface 40. First and second substrate layers 21 and 25 may be bonded using any known bonding agent, such as a suitable epoxy, or other material. Second substrate layer 25 is bonded to first substrate layer 21 to form a lid over first substrate layer 21 and to enclose detector array 12 in vacuum 32. Although second substrate layer 25 is depicted as including a single piece of substrate material, it is generally recognized that second substrate layer 25 may be two or more layers bonded together. Thus, second substrate layer 25 may comprise a ring or other spacer on the order of 400 to 800 microns in thickness supporting a lid layer. Although the top of the lid generally comprises a substrate material, the ring or other spacer could be silicon, metal, glass, or other material sufficient to support the top portion of the layer and sufficient to enclose detector array 12 in vacuum 32.

Vacuum 32 provides protection and an optimal operating environment for detector array 12 and any other enclosed elements of integrated circuit structure 30. Second substrate layer 25 may be selectively etched such that the inner portion of the sidewalls are sloped resulting in an integrated circuit 30 that includes a substantially dome-shaped vacuum space. The etching of second substrate layer 25 may be performed using photolithographic methods including photoresist mask and anisotropic etch techniques. In particular embodiments, second substrate layer 25 is on the order of 1350–1450 microns in thickness at the thickest point. Accordingly, the space within the lid structure that forms the vacuum over detector array 12 may be on the order of 700 microns in thickness and is suitably transmissive in the appropriate wavelength range. For example, second substrate layer 25 may be transmissive in the wavelength range 0.7 to 3.0 microns.

The detector array 12 enclosed within vacuum 32 includes multiple detectors 20. As described above with regard to FIGS. 1A through 1B, each detector 20 may be further divided into a sub-array of micro-detectors 22. In the illustrated embodiment, detector array 12 includes multiple bolometers for the detection of infrared light, visible light, or near ultraviolet light. Detectors 20 may be formed using typical integrated circuit fabrication techniques, such as surface micromachining using deposition and etching. Each detector 20 in detector array 12 may be on the order of 2 microns in thickness.

Although certain dimensions are used to describe the elements of FIG. 2, particular examples and dimensions specified throughout this document are intended for exemplary purposes only. The examples and dimensions disclosed are not intended to limit the scope of the present disclosure. Moreover, the figures are not intended to be to relative scale.

Figure 3A:
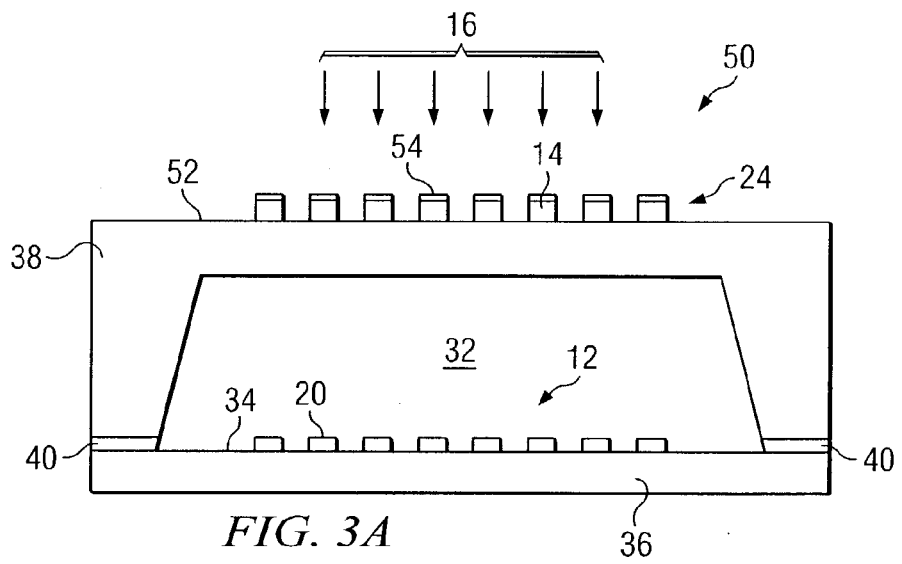
FIGS. 3A–3C are cross-sectional views of varying embodiments of an integrated circuit structure that includes one or more filters.
Figure 3B:
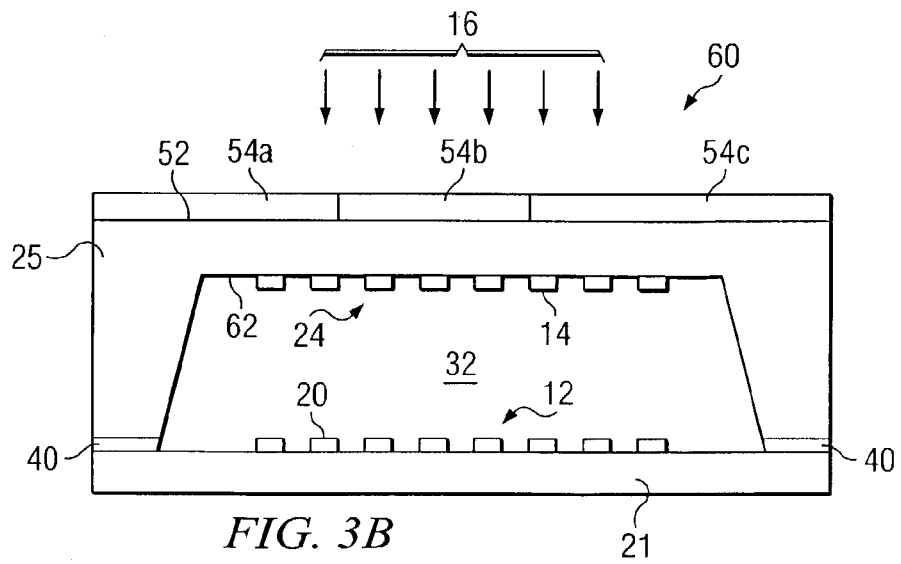
Figure 3C:
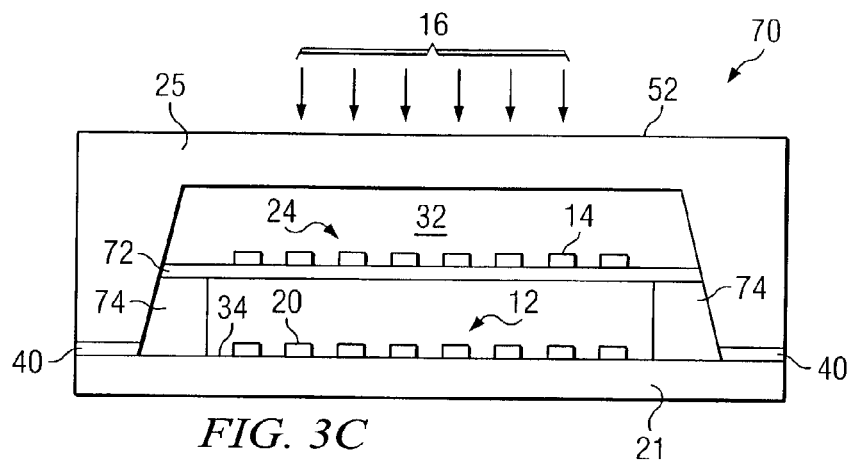

FIGS. 3A–3C are cross-sectional views of varying embodiments of an integrated circuit structure that includes one or more filters 14. The one or more filters 14 are provided proximate to second substrate layer 25 and operate, as described above, to affect the spectrum of transmitted energy 16 through filters 14. The integrated circuit structure 50 specifically shown in FIG. 3A illustrates the one or more filters 14 mounted or formed on the outer surface 52 of second substrate layer 25. Providing the filters 14 on the outside of integrated circuit 50 allows versatility in that the filters 14 may be easily replaced.

In the illustrated embodiment, integrated circuit structure 50 also includes one or more biosensitive and/or chemical sensitive patches 54 positioned proximate to filters 14. Biosensitive and/or chemical sensitive patches 54 may be comprised of a suitable polymer, which is selectively reactive to a particular wavelength or range of wavelengths within the spectrum of energy 16. For example, a particular polymer may specifically be chosen due to its tendency to affect the transmissivity of energy 16 or for the tendency of the polymer and any antibody in the polymer to be affected by reactions with biological agents or gases in a surrounding environment. Such polymers may be chosen to be specifically reactive to a particular wavelength or wavelength range where the particular wavelength or wavelength range indicates an environment including various toxins and viruses, chemical warfare agents pollutants, industrial gases, volatile organic compounds, or another biological agent. In the illustrated example, a biosensitive and/or chemical sensitive patch 54 is shown corresponding to each filter 14. Thus, the number of biosensitive and/or chemical sensitive patches is equal to M. Although the number of biosensitive and/or chemical sensitive patches 54 may correspond to the number of filters 14 in filter array 24, the number of biological patches 54 and filters 14 need not be equal. Accordingly, each biosensitive and/or chemical sensitive patch 54 may correspond to two or more filters 14, or a single filter 14 may correspond to two or more biosensitive and/or chemical sensitive patches 54.

In operation, biosensitive and/or chemical sensitive patch 54 may react when the biological agent or gas comes in contact with biosensitive and/or chemical sensitive patch 54. For example, biosensitive and/or chemical sensitive patch 54 may indicate the presence of the biological agent by changing colors or by becoming cloudy. As a result of this change, biosensitive and/or chemical sensitive patch 54 may affect the spectrum of transmitted energy through biosensitive and/or chemical sensitive patch 54 and any corresponding filters 14. Accordingly, as transmitted energy 16 is directed toward integrated circuit structure 50, transmitted energy 16 penetrates a biosensitive and/or chemical sensitive patch 54 mounted or otherwise positioned on the outer surface of a filter 14. In its changed state, biosensitive and/or chemical sensitive patch 54 may act to block a particular wavelength or range of wavelengths from passing through biosensitive and/or chemical sensitive patch 54. Thus, biosensitive and/or chemical sensitive patch 54 acts to filter the transmitted energy 16 as it enters spectroscopic system 10. Accordingly, the spectrum of transmitted energy 16 may be notched such that biosensitive and/or chemical sensitive patch 54 reflects a particular wavelength or wavelength range, while other wavelengths are transmitted through the biosensitive patch 54. That portion of transmitted energy 16 passing through biosensitive and/or chemical sensitive patch 54 may then pass through one or more corresponding filters 14. Filters 14 may further block the spectrum of transmitted energy 16. Alternatively, all wavelengths of transmitted energy 16 that passed through biosensitive and/or chemical sensitive patch 54 may be transmitted through filters 14. As such, biosensitive and/or chemical sensitive patch 54 may act as a filter, and filters 14 may be eliminated from spectroscopic system 10. After passing through biosensitive and/or chemical sensitive patch 54 and/or filter 14, transmitted energy 16 is then directed at detector array 12, which recognizes the presence or absence of a particular wavelength or wavelength range. As described above with regard to FIG. 1A, the information gathered by detector array 12 may be transmitted to a processor via read-out circuitry 18. The processor may use the information obtained from detector array 12 and biosensitive and/or chemical sensitive patches 54 to generate multi-spectrum imagery and/or trigger alarms.

FIG. 3B illustrates an integrated circuit structure 60 that includes one or more filters 14 mounted or formed on the inner surface 62 of second substrate layer 25. Filters 14 may be bonded to inner surface 62 using an epoxy or other bonding agent. Because filters 14 are mounted on the inside of integrated circuit structure 60, filters 14 are protected within vacuum 32. Locating filters 14 on the inside of integrated circuit structure 60, however, does not materially affect the operation and functionality of filters 14. Thus, filters 14 may perform substantially as described above with regard to FIGS. 1A and 3A.

Integrated circuit structure 60 also includes one or more biosensitive and/or chemical sensitive patches 54 disposed on outer surface 52 of integrated circuit structure 60. Although biosensitive and/or chemical sensitive patches 54 and filters 14 are separated by second substrate layer 25, the operation and functionality of biosensitive and/or chemical sensitive patches 54 is not altered. Thus, biosensitive and/or chemical sensitive patches 54 may operate substantially as described above with regard to FIG. 3A. Further, although integrated circuit structure 60 is shown with three biosensitive and/or chemical sensitive patches 54a–c, integrated circuit structure 60 may include any number of biosensitive and/or chemical sensitive patches 54 to detect a combination of gases and/or biological agents. Biosensitive and/or chemical sensitive patches 54 may be applied to the entire outer surface 52 of second substrate layer 25, as shown, or may be applied to only a portion of outer surface 52. Moreover, biosensitive and/or chemical sensitive patches 54 need not be placed on the outside of integrated circuit 60. Rather biosensitive and/or chemical sensitive patches 54 may be mounted proximate to filters 14 substantially as described with regard to FIG. 3A. In such an embodiment, biosensitive and/or chemical sensitive patches 54 may be adjacent to inner surface 62 of second substrate layer 25 or biosensitive and/or chemical sensitive patches 54 may be positioned on the underside of filters 14 to be proximate to detector array 12. By positioning biosensitive and/or chemical sensitive patches 54 on the outside of integrated circuit 60, however, biosensitive and/or chemical sensitive patches 54 are easily accessible for removal or replacement, and integrated circuit 60 may be reused. Accordingly, integrated circuits 60 may be mass produced and individually customized to detect particular portions of the spectrum of energy 16 by the application of particular biosensitive and/or chemical sensitive patches 54 on outer surface 52 of integrated circuit 70.

FIG. 3C illustrates an integrated circuit structure 70 that includes filters 14 mounted or formed on an intermediate substrate layer 72 within vacuum 32. Intermediate substrate layer 72 is supported by one or more spacers 74 formed on outer surface 40 of first substrate layer 21. The array of detectors 12 is positioned between first substrate layer 21 and intermediate substrate layer 72.

In the illustrated example, intermediate substrate layer 72 is supported by two spacers 74 positioned beneath opposing ends of intermediate substrate layer 72. Spacers 74 preferably comprise a dielectric and may include any suitable material used in integrated circuit fabrication, such as silicon, germanium, gallium arsenide, or other suitable material. Similarly, intermediate substrate layer 72 also comprises a dielectric and may include silicon, germanium, gallium arsenide, or other suitable material. For purposes of teaching aspects of the present invention, an exemplary embodiment will be described that includes spacers 74 and intermediate substrate layer 72 comprised of silicon oxide. Spacers 74 for infrared detection may be approximately 10 microns in thickness. In particular embodiments, for example, detectors 20 in detector array 12 are on the order of 2 microns in thickness, and intermediate substrate layer 72 is one the order of 250 microns in thickness. The stated dimensions, however, are merely provided for exemplary purposes. The elements of integrated circuit structure 70 may include any dimensions sufficient for enclosing detector array 12, intermediate substrate layer 72, and filters 14 within vacuum 32.

Spacers 74 may be grown or formed as a part of integrated circuit 70. Alternatively, spacers 74 may be bonded to outer surface 40 by epoxy or some other bonding agent. Where spacers 74 are bonded to outer surface 40 before second substrate layer 25 is bonded to outer surface 40, two different bonding agents may be used. The different bonding agents may include a high temperature bonding agent and a low temperature bonding agent. For example, the bonding agent adhering spacers 74 to outer surface 40 may be affected at a higher temperature. Conversely, the bonding agent adhering second substrate layer 25 to first substrate layer 21 may be affected at a lower temperature. Because the second bonding process is at a lower temperature, the bonding of first and second substrate layers 21 and 25 may not affect the integrity of the bond used to adhere spacers 74 to first substrate layer 21.

As described above, filters 14 are disposed proximate to intermediate substrate layer 72 and is supported on spacers 74 within vacuum 32. Filters 14 may operate substantially as described above with regard to FIG. 1A. Although integrated circuit structure 70 is depicted without biosensitive and/or chemical sensitive patches 54, biosensitive and/or chemical sensitive patches 54 may be applied to the outer surface of filters 14 as was described with regard to FIG. 3A. Alternatively biosensitive and/or chemical sensitive patches 54 may be applied to the outer surface 52 of second substrate layer 25.

Figure 4A:
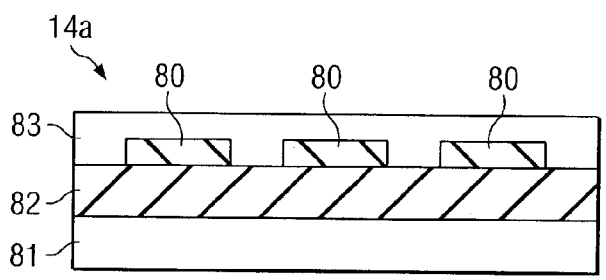
FIGS. 4A–4C are cross-sectional views of varying embodiments of a filter.
Figure 4B:
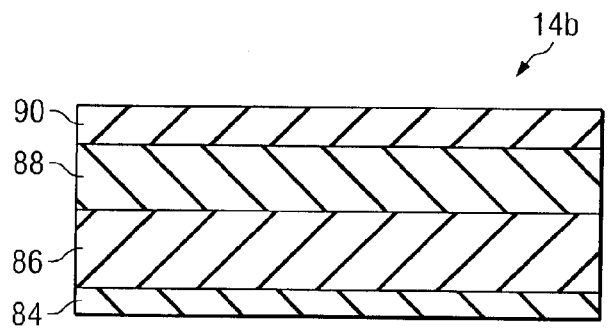
Figure 4C:
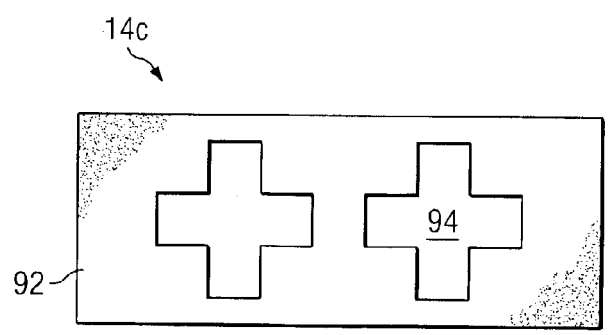

FIGS. 4A–4C are cross-sectional views of varying embodiments of a filter 14. In FIG. 4A, filter 14a includes a resonant waveguide grating of one or more dielectric towers 80 formed on one or more dielectric support layers. Although the illustrated filter 14a includes two layers of dielectric support 81 and 82, any number of layers of dielectric support may be used to achieve desired transmission properties. Dielectric towers 80, first dielectric support layer 81, and second dielectric support layer 82 are of first, second, and third dielectric materials, respectively. First, second, and third dielectric materials may include any suitable material used in integrated circuits, such as silicon, germanium, zinc sulfide, zinc selenide, gallium arsenide, or any combination of these or other dielectric materials, so long as first, second, and third dielectric materials have different indexes of refraction from one another. For example, first dielectric material may include a high index of refraction, and second and third dielectric materials may include low indices of refraction. The dielectric materials chosen for each layer as well as the number of support layers 81 and 82 may be varied to achieve desired transmission properties. For purposes of teaching aspects of the present invention, an exemplary embodiment will be described that includes dielectric towers 80 comprised of zinc sulfide and dielectric supports 81 and 82 comprised of germanium and zinc selenide, respectively.

Although filter 14a is shown as including three dielectric towers 80 on two dielectric support layers 81 and 82, any suitable number of dielectric towers 80 and dielectric support layers 81 and 82 may be used. The spacing between each dielectric tower affects the spectrum of transmitted energy 16 as it passes through filter 14a. Thus, the filter wavelength is controlled by the grating period. For example, the lateral dimension of dielectric towers 80 as well as the spacing between dielectric towers 80 may be selected to block certain wavelengths or wavelength ranges from passing through filter 14a. Accordingly, the number of dielectric towers 80 and the dimensions of dielectric towers 80 may vary depending on the particular wavelength or range of wavelengths to be filtered by filter 14a. For example, for very narrow band filters, dielectric towers may have a thickness on the order of 0.5 to 2 microns. The lateral dimensions of dielectric towers may be on the order of 2 to 3 microns in each direction, and the distance between dielectric towers may be on the order of 0.5 to 3 microns. As such, the spacing between dielectric towers 80 may be selected to affect the spectrum of transmitted energy 16 through filter 14a. The thickness of dielectric supports 81 and 82 may also be selected to affect the spectrum of transmitted energy 16 as it passes through filter 14a. Accordingly, the thickness of dielectric supports 81 and 82 may be selected independently to account for the indexes of refraction of each support dielectric layer 81 and 82. For example, the thickness of each dielectric support 81 and 82 may be on the order of 0.5 to 2 microns.

As illustrated in FIG. 4a, filter 14a includes a third dielectric support layer 83, which is formed to substantially surround dielectric towers 80. Third dielectric support layer 83 may also include any suitable material used in integrated circuits, such as silicon, germanium, zinc sulfide, zinc selenide, gallium arsenide, or any combination of these or other dielectric materials. The material selected for third dielectric support layer 83 may be dependent upon the material selected to comprise dielectric towers 80. Where, for example, it is desirable that filter 14a perform as a polarizing filter, dielectric towers 80 may comprise a material of a high index of refraction, such as germanium, and third dielectric support layer 83 may comprise a material having a low index of refraction, such as zinc sulfide. Alternatively, where polarization is not suitable, dielectric towers 80 may comprise a material of a low index of refraction, such as zinc sulfide, and air may surround dielectric towers 80. In the non-polarizing example, third dielectric layer 83 may be omitted from filter 14a.

FIG. 4B illustrates an alternate embodiment for a filter 14 in spectroscopic system 10. In this example, filter 14b includes a plurality of dielectric layers and is specifically shown as including four layers of dielectric material: first dielectric layer 84, second dielectric layer 86, third dielectric layer 88, and fourth dielectric layer 90. As illustrated, each dielectric layer 84-90 is of a varying thickness depending on the index of refraction of each dielectric material used. Thus, where the overall thickness of filter 14b is on the order of 5 microns, each dielectric layer 84-90 may be on the order of 0.1 to 1.0 microns in thickness for infrared energy. In alternative embodiments, the thickness of each dielectric layer 84-90 may be individually selected to achieve different effects on the spectrum of transmitted energy 16.

In various embodiments, each dielectric layer 84-90 may be of a different dielectric material. Accordingly, a first dielectric layer 84 is of a first dielectric material, a second dielectric layer 86 is of a second dielectric material, and so on. In alternate embodiments, filter 14b may comprise alternating layers of dielectric material. Thus, first and third dielectric layers 84 and 88 may be of a first dielectric material, and second and fourth dielectric layers 86 and 90 may be of a second dielectric material. Example dielectric materials that may be used to form filter 14a include silicon, germanium, gallium arsenide, zinc sulfide, or other suitable materials. For purposes of teaching aspects of the present invention, an exemplary embodiment will be described that includes first and third layers 84 and 88 comprised of germanium and second and fourth layers 86 and 90 comprised of zinc sulfide. In operation, the alternating layers of dielectric material operate to filter out specific wavelengths of energy by creating interference patterns dependent on the depths of the constituent layers and the respective coefficients of refraction for each dielectric layer.

FIG. 4C illustrates a filter 14C that includes a grating. The grating comprises a sheet 92 formed to include one or more apertures 94. Sheet 92 may be of aluminum, tin, or any other appropriate metal suitable for blocking the transmission of energy 16 through filter 14C. In particular embodiments, sheet 92 may be on the order of 2 microns in thickness for infrared energy. The shape and spacing of apertures 94 may be selected to allow the transmission of specific wavelengths of energy 16 through filter 14C as desired. Although filter 14C is illustrated as including apertures 94 that are substantially cross-shaped, apertures 94 may be in the shape of circles, slots, rectangles, or any other suitable shape for affecting transmitted energy 16 as desired. In operation, energy 16 is directed at filter 14C of an integrated circuit structure. A first portion of transmitted energy 16 is deflected by sheet 92. A second portion of transmitted energy 16 passes through aperture 94 such that a skewed shadow of transmitted energy 16 is directed at detector array 12. Detector array 12 is operable to detect the presence or absence of particular wavelengths of transmitted energy 16 from the skewed shadow.

Although FIGS. 4A, 4B, and 4C illustrate filters 14 that include dielectric gratings, alternating dielectric layers, and a metal grating, respectively, it is generally recognized that any other known filtering method may be alternatively used. Additionally, in particular embodiments, filters 14a may include polarizing filters. Polarization affects the propagation of EM fields at infrared, visible, ultraviolet, and X-ray wavelengths. In ordinary visible light, there are numerous wave components at random polarization angles. When transmitted light is passed through a polarizing filter, the filter blocks all light except that having a certain polarization. Accordingly, a polarizing filter affects the spectrum of transmitted energy 16 that reaches detector array 12 is affected to enable detector array 12 to detect the presence or absence of particular wavelengths within the spectrum and create imagery of a specific polarization.

Figure 5:
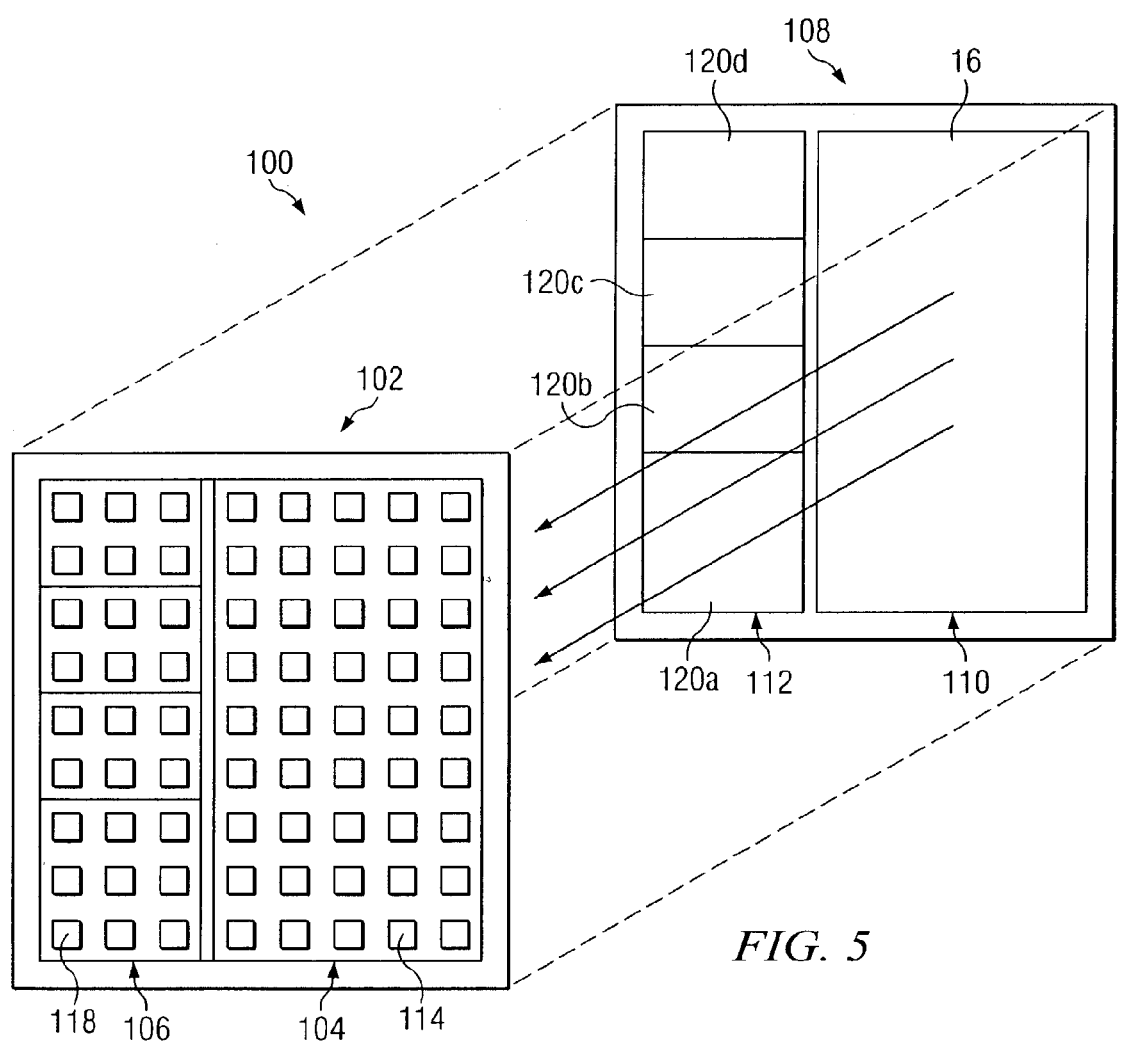
FIG. 5 is a schematic drawing of an integrated circuit for simultaneously performing spectroscopy and imaging.

FIG. 5 is a schematic drawing of an integrated circuit 100 for simultaneously performing spectroscopy and imaging. Integrated circuit 100 includes a detector plane 102 comprising an image detector array 104 and a spectroscopy detector array 106. Proximate to detector plane 102 is a filter plane 108, which includes an image filter array 110 and a spectroscopy filter array 112. Image filter array 110 of filter plane 108 corresponds generally to image detector array 104 of detector plane 102. Similarly, spectroscopy filter array 112 corresponds generally to spectroscopy detector array 106. Accordingly, energy 16, such as infrared, transmitted through image filter array 110 is substantially directed through image detector array 104. Energy 16 transmitted through spectroscopy filter array 112 is substantially directed through spectroscopy detector array 106.

Image filter array 108 includes a sub array of filters. Each filter in image filter array 108 is chosen to filter specific wavelengths or wavelength ranges in the spectrum of transmitted energy 16. The filters may affect the spectrum of transmitted energy 16 by blocking a particular wavelength range or by blocking all wavelengths outside this particular wavelength range. For example, image filter array 110 may include three types of filters and each type of filter may operate to block the transmission of energy 16 outside a particular wavelength range. A first filter type may block all transmitted energy that is outside the short wavelength infrared range (0.7 to 3.0 microns). Accordingly, only transmitted energy in the 0.7 to 3.0 micron range may pass through this type of filter. A second filter type may block all transmitted energy that is outside the medium wavelength infrared range (3 to 5 microns) allowing only energy within the medium range to pass through the filter. And, a third filter type may block all transmitted energy that is outside the long wavelength infrared range (7 to 14 microns), blocking energy within either the short or medium wavelength ranges from passing through the filter. The filtering of energy 16 into different short, medium, and long wavelength bands allows for the creation of multi-spectrum imagery. Multi-spectrum imagery, or polychromatic imagery, is composed of radiation of more than one wavelength in a broader band of wavelengths. Thus, polychromatic imagery may include energy 16 radiating in more than one color in the spectrum. In specific examples, transmitted energy 16 may be filtered for use in the creation of multi-color imagery.

In another example, image filter array 110 may include a single type of filter. The filters may include pass-band filters that operate to block only that portion of energy 16 that is not infrared. Thus, the filters may operate to block visible light and ultraviolet light, allowing only infrared light within energy 16 to pass through the filters. The filtering of transmitted energy 16 in this manner allows for the creation of monochromatic imagery. Monochromatic imagery is composed of radiation of a very narrow band of wavelengths. Because monochromatic imagery includes all intensity levels within the narrow band of wavelengths, monochromatic imagery may be used to detect subtle distinctions in hues and tint. For example, transmitted energy 16 may be filtered such that a narrow band of wavelengths is detected for use in the creation of night imagery.

Spectroscopy filter array 112 includes one or more filters 120 that are chosen to filter a specific wavelength corresponding to a particular biological agent or a targeted vapor, chemical, or gas. As described with regard to FIGS. 3A–C, biological agents, chemical agents, vapors, and gases are known to emit a particular wavelength. For example, if carbon monoxide absorbs at a wavelength of 4.6 microns, a filter 120a may be chosen to transmit only 4.6 micron wavelengths in the spectrum of energy 16. All other wavelengths may be deflected by filter 120a. Filters 120a–d may be selected to transmit wavelengths diverse to one another to detect additional biological agents or targeted vapors, chemicals, and gases. Thus, filter 120b may be selected because it transmits the particular wavelength range absorbed by a particular toxin or virus. Conversely, filters 120c and 120d may be selected because the filters transmit the particular wavelengths emitted by volatile organic compounds and a particular chemical warfare agent, pollutant, or industrial gas, respectively. In this manner, a single integrated circuit 100 may act to detect multiple biological agents, vapors, chemicals, or gases.

In particular embodiments, in addition to allowing the particular wavelength to pass through filter 120a, filter 120a may also be reactive to the particular wavelength. As was described with regard to FIG. 1A, filter 120a may indicate the presence of the targeted vapor, chemical, gas, or biological agent by turning cloudy or by turning a particular color also associated with the particular wavelength.

Image detector array 106 includes multiple detectors 114, each of which may further comprise a sub-array of micro-detectors. The number of detectors 114 or micro-detectors need not necessarily correspond to the number of filters included in image filter array 110. Rather, the ratio of filters to detectors 114 may be many to one. Detectors 114 operate to detect the presence or absence of a wavelength or range of wavelengths in a transmitted energy 16 to produce an image array. Accordingly, a detector 114 proximate to and receiving energy 16 transmitted through a filter in filter array 110 that operates to block all wavelengths of energy 16 outside the short wavelength range, may detect the presence of wavelengths between 0.7 and 3.0 microns, but fail to detect all other wavelengths within the spectrum of transmitted energy 16. Detectors 114 proximate to and receiving energy 16 passing through filters operating to allow the transmission of other wavelength ranges, i.e. medium or long, may operate similarly. An image array may be created from the detection of particular wavelengths by each detector 114. As was described with regard to FIG. 1A, the image array may be transmitted to a processor via read-out circuitry 18 (not shown) for the production of color or non-color imagery.

Spectroscopy detector array 106 also includes multiple detectors 118, each of which may comprise a sub-array of micro-detectors. Although detectors 118 also operate to detect the presence or absence of a wavelength or range of wavelengths in a spectrum of transmitted energy 16, information obtained by detectors 118 is used for spectroscopy to detect the presence of biological agents or target vapors, chemicals, or gases that emit the particular wavelength or wavelength range detected to be present or absent.

Figure 6:
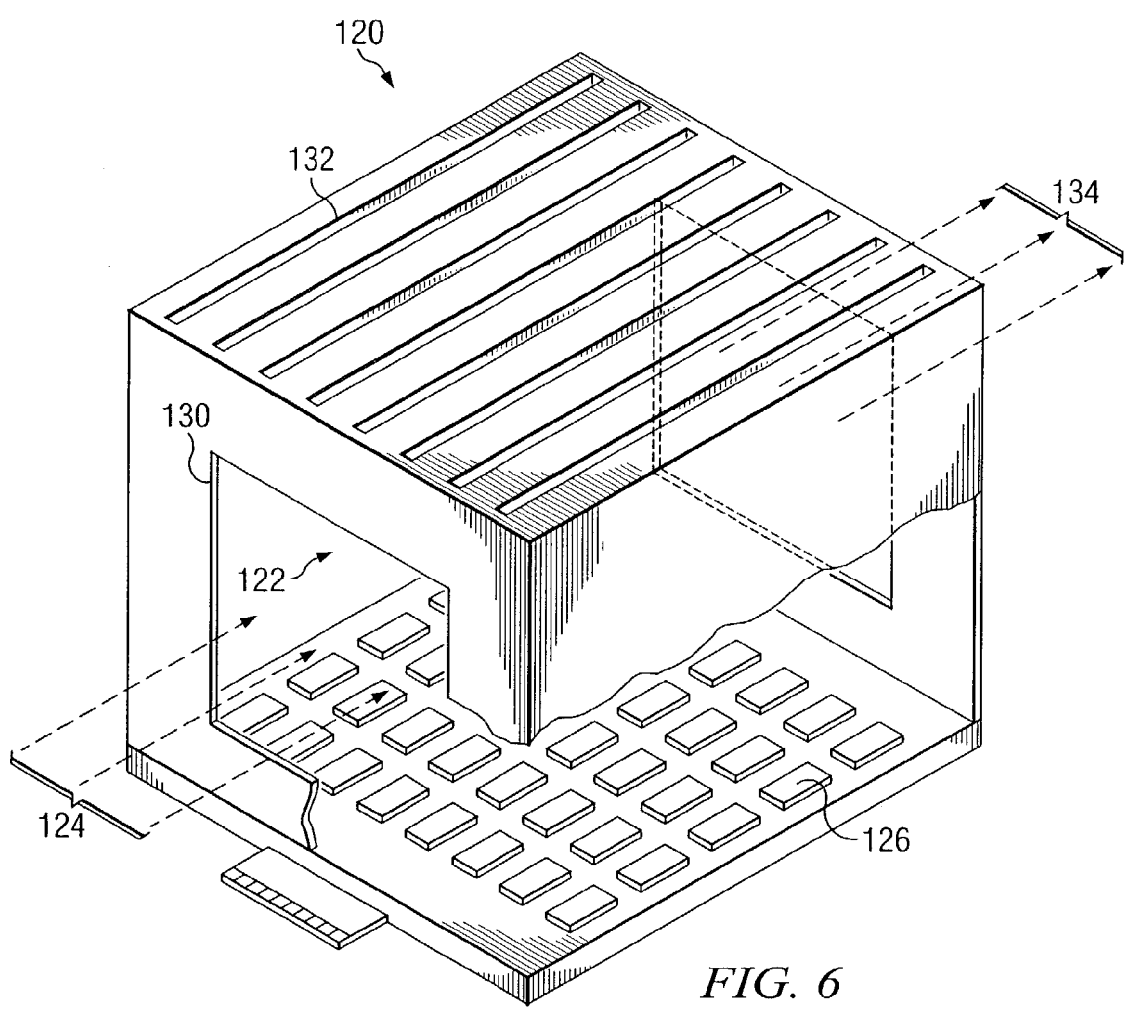
FIG. 6 is a schematic drawing of a spectroscopic system for detecting target vapors, chemicals, and gases.

FIG. 6 is a schematic drawing of a spectroscopic system 120 for detecting target gases. Spectroscopic system 120 includes a chamber 122, airflow 124, a detector and filter array 126, and a light source 132. Detector and filter array 126 includes a plurality of detectors (not shown) and filters (not shown). Each detector and filter may be substantially as described with regard detectors 20 of FIGS. 1A through 3C. Thus, in particular embodiments, detector and filter array 126 may include multiple single pixel detectors using a bolometer comprised of amorphous silicon. Filters within the detector and filter array 126 are mounted adjacent the detectors and operate to affect the spectrum of infrared light 132 directed at detector and filter array 126. Each filter may be substantially as described above with regard to filters 14 of FIGS. 1A through 4C. Chamber 122 blocks outside light from impinging on the detector and filter array 126, but includes light source 132 to permit infrared light to enter chamber 122. Chamber 122 also includes one or more perforations 130 in the walls or ceiling of chamber 122 to permit target gases and other biological agents to enter and flow through as depicted by arrows 124 and 134. As the target gases or other biological agents flow through chamber 122, chamber 122 reflects the ambient gas composition or biological composition.

In operation, spectroscopic system 120 may detect the presence of gases such as carbon monoxide, hydrogen sulfide, ozone, or other target gases. Alternatively or additionally, spectroscopic system 129 may detect biological agents such toxins and viruses, chemical warfare agents, pollutants, industrial gases, VOC, or other biological agents. Because such gases and biological agents fall within known wavelength ranges, the filters in detector and filter array 126 may be selected to react when the gases and biological agents are present in chamber 122. In particular embodiments, detector and filter array 126 may operate to detect the presence of a particular wavelength of light corresponding to a particular gas or biological agent. Alternatively, detector and filter array 126 may operate to detect the absence of a particular wavelength of light corresponding to a particular gas or biological agent. Thus, if in the first example, carbon monoxide transmits at a wavelength of 4.6 microns, and carbon monoxide enters chamber 122, infrared light 124 directed at the carbon monoxide may filtered by the filters of detector and filter array 126, allowing only that portion of infrared light 132 of a wavelength of 4.6 microns to be detected by detector and filter array 126. In the alternate example, filters in detector and filter array 126 may act to block only infrared light 132 of a wavelength of 4.6 microns, and all other wavelengths of infrared light 132 may pass through the filters to be detected by the detectors of detector and filter array 126. Detector and filter array 126 may then detect the presence or absence of the particular wavelength, as appropriate, to determine the presence of carbon monoxide in the environment.

Although the present invention has been described in detail, it should be understood that various changes, alterations, substitutions, and modifications can be made to the teachings disclosed herein without departing from the spirit and scope of the present invention which is solely defined by the appended claims.

What is claimed is:

1. A method for forming an integrated circuit, comprising:
   providing an array of detectors proximate an outer surface layer of an integrated circuit, the array of detectors operable to detect the presence or absence of one or more wavelengths within a spectrum of transmitted energy;
   providing one or more filters proximate a substrate layer, the one or more filters operable to affect the spectrum of transmitted energy through the one or more filters; and
   coupling the substrate layer to the outer surface layer of the integrated circuit to enclose the array of detectors in a vacuum environment and form a packaged integrated circuit structure.

2. The method of claim 1, wherein each detector in the array of detectors comprises a sub-array of bolometers.

3. The method of claim 1, wherein providing one or more filters proximate the substrate layer comprises forming one or more filters proximate an outer surface of the substrate layer.

4. The method of claim 1, wherein providing the one or more filters proximate the substrate layer comprises forming one or more filters proximate an inner surface of the substrate layer, the one or more filters enclosed within the vacuum.

5. The method of claim 1, wherein providing the one or more filters proximate the substrate layer comprises:
   disposing one or more spacers proximate the outer surface layer of the integrated circuit;
   disposing an intermediate substrate layer on the one or more spacers, the intermediate substrate layer supported by the one or more spacers, the array of detectors positioned between the outer surface layer of the integrated circuit and the intermediate substrate layer; and
   providing one or more filters proximate the intermediate substrate layer, the one or more filters enclosed within the vacuum.

6. The method of claim 1, wherein each filter comprises a plurality of alternating dielectric layers, the first dielectric layer comprising a first dielectric material, the second dielectric layer comprising a second dielectric material.

7. The method of claim 1, wherein the one or more filters comprise a sheet of metal including one or more apertures formed therein.

8. The method of claim 1, wherein the one or more filters comprise one or more dielectric towers formed proximate one or more dielectric support layers, the height and spacing of the dielectric towers selected to affect the spectrum of transmitted energy through the one or more filters.

9. The method of claim 1, wherein the one or more filters comprise one or more polarizing filters.

10. The method of claim 1, wherein the integrated circuit is operable to determine the presence of a gas from a presence or absence of the one or more wavelengths within the spectrum.

11. The method of claim 1, further comprising providing one or more biosensitive patches proximate an outer surface of the substrate layer, the one or more biosensitive patches affected by the transmission of energy to detect a biological agent.

12. The method of claim 1, further comprising providing one or more biosensitive patches proximate an outer surface of the one or more filters, the one or more biosensitive patches affected by the transmission of energy to detect a biological agent.

13. The method of claim 1, wherein the integrated circuit is operable to perform imaging and spectroscopy.

14. A method of spectroscopy, comprising:
   directing a spectrum of transmitted energy at an integrated circuit, the integrated circuit comprising an array of detectors provided proximate an outer surface of an integrated circuit substrate layer and a lid substrate layer coupled to the outer surface of the integrated circuit substrate layer to enclose the array of detectors in a vacuum environment and form a packaged integrated circuit structure, the second substrate layer comprising one or more filters operable to filter affect the spectrum of transmitted energy through the one or more filters; and
   detecting the presence or absence of one or more wavelengths within the spectrum.

15. The method of claim 14, wherein each detector in the array of detectors comprises a sub-array of bolometers.

16. The method of claim 14, wherein the one or more filters are disposed proximate an outer surface of the lid substrate layer.

17. The method of claim 14, wherein the one or more filters are disposed proximate an inner surface of the lid substrate layer, the one or more filters enclosed within the vacuum.

18. The method of claim 14, wherein the one or more filters are disposed proximate an intermediate substrate layer supported by one or more spacers proximate the outer surface of the integrated circuit substrate layer, the array of detectors positioned between the integrated circuit substrate layer and the intermediate substrate layer, the one or more filters enclosed within the vacuum.

19. The method of claim 14, wherein each filter comprises a plurality of alternating dielectric layers, the first dielectric layer comprising a first dielectric material, the second dielectric layer comprising a second dielectric material.

20. The method of claim 14, wherein the one or more filters comprise a sheet of metal including one or more apertures formed therein.

21. The method of claim 14, wherein the one or more filters comprise one or more dielectric towers formed proximate one or more dielectric support layers, the height and spacing of the dielectric towers selected to affect the spectrum of transmitted energy through the one or more filters.

22. The method of claim 14, wherein the one or more filters comprise one or more polarizing filters.

23. The method of claim 14, further comprising determining the presence of a gas from a detection of a presence or absence of the one or more wavelengths within the spectrum.

24. The method of claim 14, further comprising providing one or more biosensitive patches proximate an outer surface of the lid substrate layer, the one or more biosensitive patches affected by the transmission of energy to detect a biological agent.

25. The method of claim 14, further comprising providing one or more biosensitive patches proximate an outer surface of the one or more filters, the one or more biosensitive patches affected by the transmission of energy to detect a biological agent.

26. The method of claim 14, wherein the integrated circuit is operable to perform imaging and spectroscopy.

27. An integrated circuit for spectroscopy, comprising:
an array of detectors provided proximate an outer surface layer of the integrated circuit, the array of detectors operable to detect the presence or absence of one or more wavelengths within a spectrum of transmitted energy;
a lid substrate layer coupled to the outer surface layer of the integrated circuit to enclose the array of detectors in a vacuum environment and form a packaged integrated circuit; and
one or more filters provided proximate the lid substrate layer, the one or more filters operable to affect the spectrum of transmitted energy through the filter.

28. The integrated circuit of claim 27, wherein each detector in the array of detectors comprises a sub-array of bolometers.

29. The integrated circuit of claim 27 wherein the one or more filters are formed proximate an outer surface of the lid substrate layer.

30. The integrated circuit of claim 27, wherein the one or more filters are formed proximate an inner surface of the lid substrate layer, the one or more filters enclosed within the vacuum.

31. The integrated circuit of claim 27, wherein the one or more filters are disposed proximate an intermediate substrate layer supported by one or more spacers proximate the outer surface layer of the integrated circuit, the array of detectors positioned between the outer surface layer of the integrated circuit and the intermediate substrate layer, the one or more filters enclosed within the vacuum.

32. The integrated circuit of claim 27, wherein each filter comprises a plurality of alternating dielectric layers, the first dielectric layer comprising a first dielectric material, the second dielectric layer comprising a second dielectric material.

33. The integrated circuit of claim 27, wherein the one or more filters comprise a sheet of metal including one or more apertures formed therein.

34. The integrated circuit of claim 27, wherein the one or more filters comprise one or more dielectric towers formed proximate one or more dielectric support layers, the height and spacing of the dielectric towers selected to affect the spectrum of transmitted energy through the one or more filters.

35. The integrated circuit of claim 27, wherein the one or more filters comprise one or more polarizing filters.

36. The integrated circuit of claim 27, wherein the array of detectors is further operable to determine the presence of a gas from a presence or absence of the one or more wavelengths within the spectrum.

37. The integrated circuit of claim 27, further comprising one or more biosensitive patches proximate an outer surface of the lid substrate layer, the one or more biosensitive patches affected by the transmission of energy to detect a biological agent.

38. The integrated circuit of claim 27, further comprising one or more biosensitive patches proximate an outer surface of the one or more filters, the one or more biosensitive patches affected by the transmission of energy to detect a biological agent.

39. The integrated circuit of claim 27, wherein the integrated circuit is operable to perform imaging and spectroscopy.

* * * * *